(12) United States Patent
Cooper

(10) Patent No.: US 9,339,341 B2
(45) Date of Patent: May 17, 2016

(54) DIRECT PULL SURGICAL GRIPPER

(75) Inventor: Thomas G. Cooper, Menlo Park, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 947 days.

(21) Appl. No.: 12/702,200

(22) Filed: Feb. 8, 2010

(65) Prior Publication Data
US 2011/0196419 A1   Aug. 11, 2011

(51) Int. Cl.
*A61B 17/00*   (2006.01)
*A61B 19/00*   (2006.01)
(Continued)

(52) U.S. Cl.
CPC .............. *A61B 19/2203* (2013.01); *A61B 17/29* (2013.01); *A61B 18/1445* (2013.01); *A61B 2017/003* (2013.01); *A61B 2017/2932* (2013.01); *A61B 2017/2933* (2013.01); *A61B 2017/2938* (2013.01); *A61B 2017/2945* (2013.01);
(Continued)

(58) Field of Classification Search
CPC ........ A61B 10/06; A61B 17/28; A61B 17/29; A61B 17/2932; A61B 17/294; A61B 17/2934; A61B 17/2938; A61B 2019/2242; A61B 2017/2933; A61B 2017/2937; A61B 2017/2939; A61B 2017/294; A61B 2017/2941; A61B 2017/2944; A61B 2017/2947; A61B 2017/2926; A61B 2017/2919; A61B 2017/2934; A61B 2017/2932; A61B 2017/2938; B25J 7/00; B25J 9/10; B25J 15/00; B25J 15/0028; B25J 15/0206; B25J 15/0286

USPC ............. 606/50–52, 130, 205–209, 167, 174; 600/562, 564; 294/106, 111, 110.1, 294/110.2, 112; 74/490.01; 901/30–39
See application file for complete search history.

(56) References Cited

U.S. PATENT DOCUMENTS 5,373,854 A * 12/1994 Kolozsi ........................ 600/562
5,396,900 A   3/1995 Slater et al.
(Continued)

FOREIGN PATENT DOCUMENTS

JP   H11509459 A   8/1999
JP   2002503131 A   1/2002
(Continued)

OTHER PUBLICATIONS

PCT/US11/22510 International Search Report and Written Opinion of the International Searching Authority, mailed May 2, 2011, 9 pages.
(Continued)

*Primary Examiner* — Katherine M Shi
*Assistant Examiner* — Lindsey Bachman

(57) ABSTRACT

A surgical end effector includes a clevis and two jaws pivotally coupled to the clevis. A wire is coupled to each jaw and extended through a guide way in the other jaw and through an end of the clevis. The jaws may be opened and closed by pushing and pulling on the two cables. Pulling on each wire creates a closing force in both jaws. A rocking pin may be pivotally supported by the clevis and pivotally coupled to the jaws to constrain the jaws to have opposite motions. The clevis may be coupled to an elongate shaft and the wires extended through the shaft to provide an endoscopic instrument. A wire guide may support the wires in the shaft such that they are able to transmit a compressive force without buckling. The wires may carry electricity to the jaws for electrocautery.

19 Claims, 7 Drawing Sheets

(51) Int. Cl.
*A61B 17/29* (2006.01)
*A61B 18/14* (2006.01)
*A61B 18/00* (2006.01)

(52) U.S. Cl.
CPC .............. *A61B2018/00595* (2013.01); *A61B 2018/1432* (2013.01); *A61B 2019/2242* (2013.01)

(56) References Cited

U.S. PATENT DOCUMENTS

| | | | |
|---|---|---|---|
| 5,575,805 A * | 11/1996 | Li | 606/206 |
| 5,582,617 A | 12/1996 | Klieman et al. | |
| 5,792,165 A | 8/1998 | Klieman et al. | |
| 5,843,000 A * | 12/1998 | Nishioka et al. | 600/566 |
| 6,083,240 A | 7/2000 | Ouchi | |
| 6,273,860 B1 | 8/2001 | Kostylev et al. | |
| 6,394,998 B1 | 5/2002 | Wallace et al. | |
| 6,554,850 B1 | 4/2003 | Ouchi et al. | |
| 6,582,451 B1 * | 6/2003 | Marucci et al. | 606/207 |
| 6,840,938 B1 * | 1/2005 | Morley et al. | 606/51 |
| 6,964,662 B2 | 11/2005 | Kidooka | |
| 7,354,439 B2 * | 4/2008 | Kidooka | 606/51 |
| 7,648,519 B2 * | 1/2010 | Lee et al. | 606/205 |

FOREIGN PATENT DOCUMENTS

| | | |
|---|---|---|
| JP | 2004194740 A | 7/2004 |
| JP | 2004524923 A | 8/2004 |
| JP | 2005218497 A | 8/2005 |
| JP | 2010022696 A | 2/2010 |
| WO | WO9610957 A1 | 4/1996 |
| WO | WO-02080783 A1 | 10/2002 |
| WO | WO-2010009223 A2 | 1/2010 |

OTHER PUBLICATIONS

Vertut, Jean and Phillipe Coiffet, Robot Technology: Teleoperation and Robotics Evolution and Development, English translation Prentice-Hall, Inc., Inglewood Cliffs, NJ, USA 1986, vol. 3A, 332 pages.
Office Action dated Apr. 10, 2013 for U.S. Appl. No. 12/910,634.
Office Action mailed Jul. 24, 2014 for Chinese Application No. 201180008755.0 filed Jan. 26, 2011.

* cited by examiner

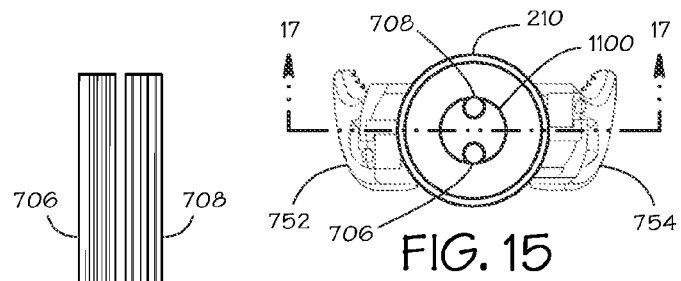
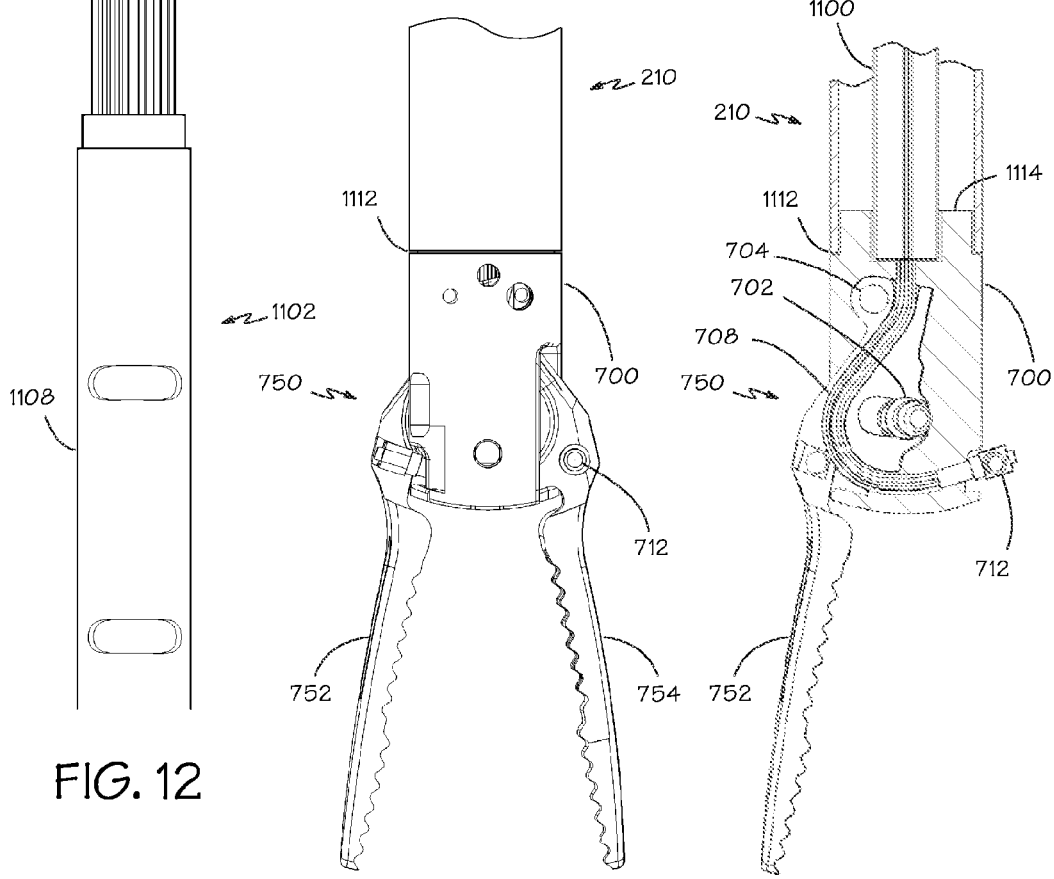
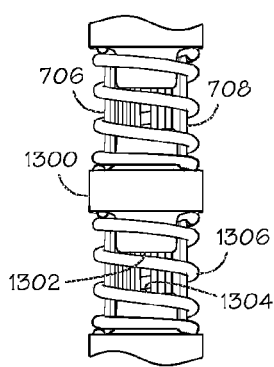
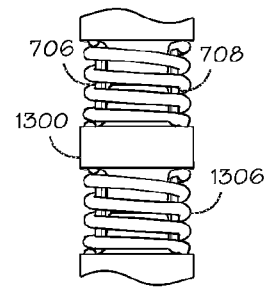
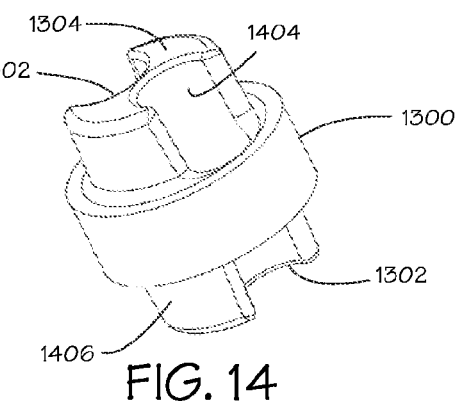
FIG. 15
FIG. 12
FIG. 16
FIG. 17
FIG. 13A
FIG. 13B
FIG. 14

DIRECT PULL SURGICAL GRIPPER

BACKGROUND

1. Field

Embodiments of the invention relate to the field of surgical instruments; and more specifically, to surgical instruments intended for use in minimally invasive surgeries.

2. Background

Minimally invasive surgery (MIS) (e.g., endoscopy, laparoscopy, thoracoscopy, cystoscopy, and the like) allows a patient to be operated upon through small incisions by using elongated surgical instruments introduced to an internal surgical site. Generally, a cannula is inserted through the incision to provide an access port for the surgical instruments. The surgical site often comprises a body cavity, such as the patient's abdomen. The body cavity may optionally be distended using a clear fluid such as an insufflation gas. In traditional minimally invasive surgery, the surgeon manipulates the tissues by using hand-actuated end effectors of the elongated surgical instruments while viewing the surgical site on a video monitor.

The elongated surgical instruments will generally have an end effector in the form of a surgical tool such as a forceps, a scissors, a clamp, a needle grasper, or the like at one end of an elongate tube. An actuator that provides the actuating forces to control the end effector is coupled to the other end of the elongate tube. A means of coupling the actuator forces to the end effector runs through the elongate tube. To minimize the size of incision needed for the instrument access port, the elongate tube is generally of a small diameter, preferably about 6 millimeters. Thus, it is necessary that the means of coupling the actuator forces to the end effector be compact.

It may be desirable that the elongate tube be somewhat flexible to allow the surgical instrument to adapt to the geometry of the surgical access path. In some cases, the elongate tube may be articulated to provide access to a surgical site that is not directly in line with the surgical access port. It may be desirable to use wires as the means of coupling the actuator forces to the end effector because of the flexibility they provide and because of the ability of a wire to transmit a significant force, a substantial distance, through a small cross-section. However, an unsupported wire is only able to transmit a force in tension. Thus it is generally necessary to provide two wires to transmit a bidirectional actuating force. This doubles the cross-section required for the wires to pass through the elongate tube.

The wires need to have sufficient strength to provide the tension necessary to create the required forces provided by the end effector. The more tension that is required, the larger the wire cross-section must be. Inefficiencies in converting wire tension into end effector forces increases the tension, and hence the cross-section, required. Increases in the cross-section, whether because of a greater number of wires or a larger cross-section of the individual cables, increases the effect of bending the cable, such as when is passes through an articulated wrist joint, on the force being delivered by the cable. This can cause changes in the clamping pressure of a surgical end effector as the end effector is moved by an articulated wrist assembly that supports the end effector.

It is also desirable to provide electrical connections to provide an electrical current for bipolar cautery in which a tissue is cauterized by current flowing through the tissue. The two connections of opposite polarity to the tissue can be provided by the two jaws of the surgical end effector. Thus it is necessary to electrically isolate one jaw from the other and provide an insulated electrical connection from each of the two jaws to the actuator end of the elongate tube where the cautery current is supplied.

In view of the above, it would be desirable to provide an improved apparatus and method for transmitting bidirectional actuating forces through an elongate tube and applying those forces to a surgical end effector of a surgical instrument intended for use in minimally invasive surgeries that reduces the cross-section required in the elongate tube and providing electrical connections for the electrical current needed for bipolar cautery.

SUMMARY

A surgical end effector includes a clevis and two jaws pivotally coupled to the clevis. A wire is coupled to each jaw and extended through a guide way in the other jaw and through an end of the clevis. The jaws may be opened and closed by pushing and pulling on the two cables. Pulling on each wire creates a closing force in both jaws. A rocking pin may be pivotally supported by the clevis and pivotally coupled to the jaws to constrain the jaws to have opposite motions. The clevis may be coupled to an elongate shaft and the wires extended through the shaft to provide an endoscopic instrument. A wire guide may support the wires in the shaft such that they are able to transmit a compressive force without buckling. The wires may carry electricity to the jaws for electrocautery.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements:

FIG. 12 is a side view of a proximal end of wires and a wire guide.

FIG. 13A is a detailed view of a compression section of the wire guide in an uncompressed condition.

FIG. 13B is a detailed view of a compression section of the wire guide in a compressed condition.

FIG. 14 is a perspective view of a wire support section from the compression section shown in FIGS. 13A and 13B.

FIG. 15 is a top view of an elongate shaft with a wire guide.

FIG. 16 is a front view of an end effector.

FIG. 17 is a section view of the end effector taken along line 17-17 of FIG. 15.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure the understanding of this description.

In the following description, reference is made to the accompanying drawings, which illustrate several embodiments of the present invention. It is understood that other embodiments may be utilized, and mechanical compositional, structural, electrical, and operational changes may be made without departing from the spirit and scope of the present disclosure. The following detailed description is not to be taken in a limiting sense, and the scope of the embodiments of the present invention is defined only by the claims of the issued patent.

The terminology used herein is for the purpose of describing particular embodiments only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

Figure 1:
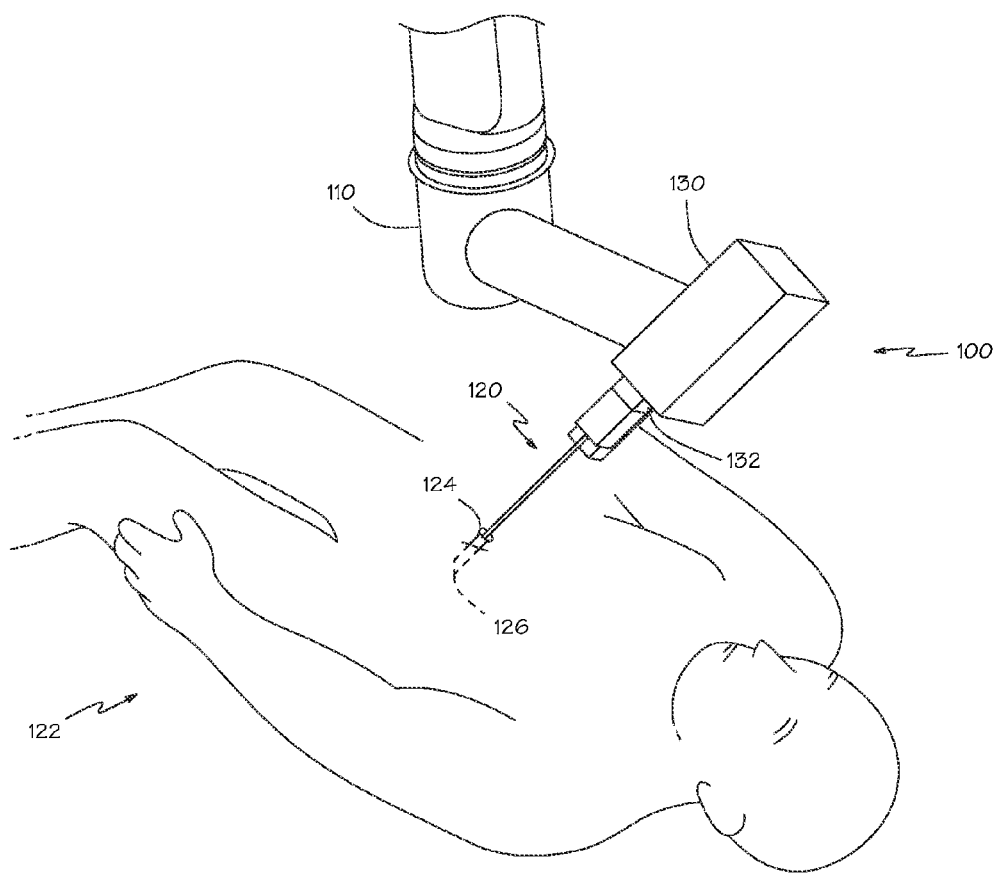
FIG. 1 is a simplified perspective view of a robotic surgical system with a robotically controlled surgical instrument inserted through a port in a patient's abdomen.

FIG. 1 is a simplified perspective view of a robotic surgical system 100, in accordance with embodiments of the present invention. The system 100 includes a support assembly 110 mounted to or near an operating table supporting a patient's body 122. The support assembly 110 supports one or more surgical instruments 120 that operate on a surgical site 126 within the patient's body 122. The term "instrument" is used herein to describe a device configured to be inserted into a patient's body and used to carry out surgical procedures. The instrument includes a surgical tool, such as a forceps, a needle driver, a shears, a bipolar cauterizer, a tissue stabilizer or retractor, a clip applier, an anastomosis device, and the like. The surgical tool used with embodiments of the invention provides some form of gripping in which one part of the tool opens and closes against another part.

The simplified perspective view of the system 100 shows only a single instrument 120 to allow aspects of the invention to be more clearly seen. A functional robotic surgical system would further include a vision system that enables the operator to view the surgical site from outside the patient's body 122. The vision system can include a video monitor for displaying images received by an optical device provided at a distal end of one of the surgical instruments 120. The optical device can include a lens coupled to an optical fiber which carries the detected images to an imaging sensor (e.g., a CCD or CMOS sensor) outside of the patient's body 122. Alternatively, the imaging sensor may be provided at the distal end of the surgical instrument 120, and the signals produced by the sensor are transmitted along a lead or wirelessly for display on the monitor. An illustrative monitor is the stereoscopic display on the surgeon's cart in the da Vinci® Surgical System, marketed by Intuitive Surgical, Inc., of Sunnyvale Calif.

A functional robotic surgical system would further include a control system for controlling the insertion and articulation of the surgical instruments 120. This control may be effectuated in a variety of ways, depending on the degree of control desired, the size of the surgical assembly, and other factors. In some embodiments, the control system includes one or more manually operated input devices, such as a joystick, exoskeletal glove, or the like. These input devices control servo motors which, in turn, control the articulation of the surgical assembly. The forces generated by the servo motors are transferred via drivetrain mechanisms, which transmit the forces from the servo motors generated outside the patient's body 122 through an intermediate portion of the elongate surgical instrument 120 to a portion of the surgical instrument inside the patient's body 122 distal from the servo motor. Persons familiar with telemanipulative, teleoperative, and telepresence surgery will know of systems such as the da Vinci® Surgical System and the Zeus® system originally manufactured by Computer Motion, Inc. and various illustrative components of such systems.

The surgical instrument 120 is shown inserted through an entry guide cannula 124, e.g., a single port in the patient's abdomen. A functional robotic surgical system may provide an entry guide manipulator (not shown; in one illustrative aspect the entry guide manipulator is part of the support system 110) and an instrument manipulator (discussed below). The entry guide 124 is mounted onto the entry guide manipulator, which includes a robotic positioning system for positioning the distal end 126 of the entry guide 124 at the desired target surgical site. The robotic positioning system may be provided in a variety of forms, such as a serial link arm having multiple degrees of freedom (e.g., six degrees of freedom) or a jointed arm that provides a remote center of motion (due to either hardware or software constraints) and which is positioned by a setup joint mounted onto a base. Alternatively, the entry guide manipulator may be manually maneuvered so as to position the entry guide 124 in the desired location. In some telesurgical embodiments, the input devices that control the manipulator(s) may be provided at a location remote from the patient (outside the room in which the patient is placed). The input signals from the input devices are then transmitted to the control system, which, in turn, manipulates the manipulators 130 in response to those signals. The instrument manipulator may be coupled to the entry guide manipulator such that the instrument manipulator 130 moves in conjunction with the entry guide 124.

The surgical instrument 120 is detachably connected to the robotic instrument manipulator 130. The robotic manipulator includes a coupler 132 to transfer controller motion from the robotic manipulator to the surgical instrument 120. The instrument manipulator 130 may provide a number of controller motions which the surgical instrument 120 may translate into a variety of movements of the end effector on the surgical instrument such that the input provided by a surgeon through the control system is translated into a corresponding action by the surgical instrument.

Figure 2:
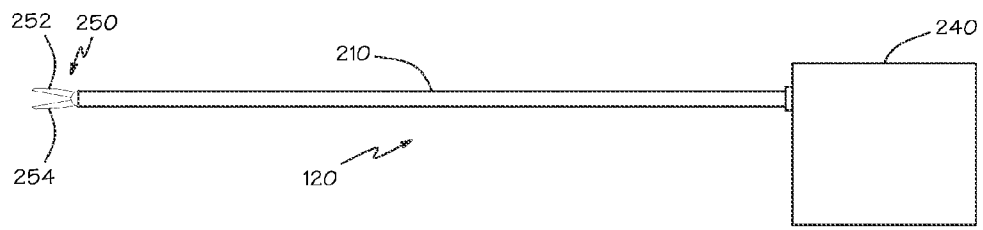
FIG. 2 is a plan view of a surgical instrument for use with a robotic manipulator.

FIG. 2 is a plan view of an illustrative embodiment of the surgical instrument 120, comprising a distal portion 250 and a proximal control mechanism 240 coupled by an elongate tube 210. The distal portion 250 of the surgical instrument 120 can provide any of a variety of surgical devices as an end effector such as the forceps shown, a needle driver, a shears, a bipolar cauterizer, a tissue stabilizer or retractor, a clip applier, an anastomosis device, and the like. Many of the surgical devices that may be provided as an end effector have a pair of jaws 252, 254 having the ability to be open and closed with a scissor-like motion. This requires that a controller motion provided by the instrument manipulator 130 be transmitted through the elongate tube 210 to effect the opening and closing of the jaws 252, 254.

Figure 3:
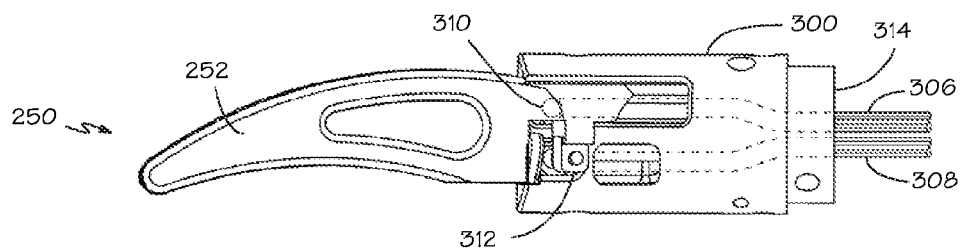
FIG. 3 is a side view of a surgical end effector.
Figure 4:
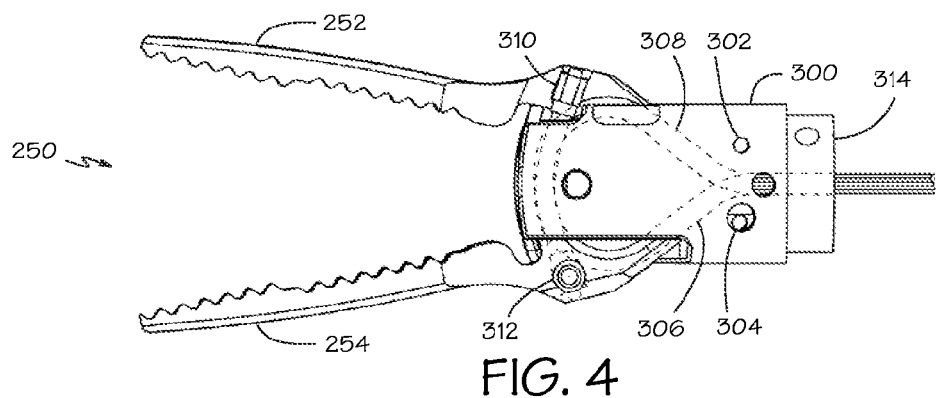
FIG. 4 is a front view of the surgical end effector of FIG. 3.
Figure 5:
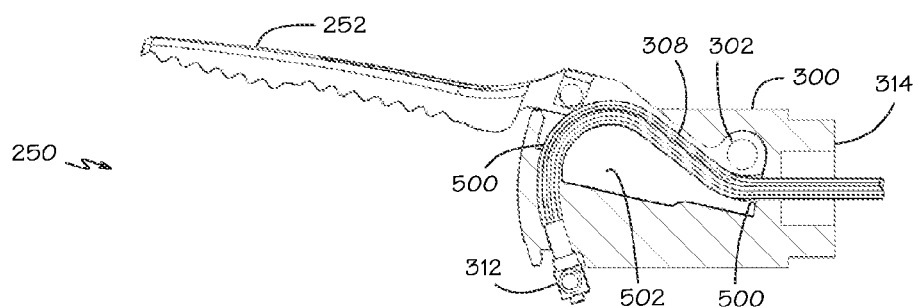
FIG. 5 is a front view of the surgical end effector of FIG. 3 with an upper portion removed to allow certain details to be seen more clearly.

FIGS. 3 through 5 show an embodiment of a surgical end effector 250. FIG. 3 shows a side view of the surgical end effector 250. FIG. 4 shows a top view of the surgical end effector 250. FIG. 5 shows a top view of the surgical end effector 250 with an upper portion removed to allow certain details to be seen more clearly.

The surgical end effector 250 includes a clevis 300 that pivotally supports the first jaw 252 and the second jaw 254. A first pivot 302 couples the first jaw 252 to the clevis 300. A second pivot 304 couples the second jaw 254 to the clevis 300. A first wire 306 is coupled to the first jaw 252 by a first fitting 310 crimped to the end of the cable. The first wire 306 extends through a guide way in the second jaw 254 and through an end of the clevis 314. A second wire 308 is coupled to the second jaw 254 by a second fitting 312 crimped to the end of the cable. The second wire 308 extends through a guide way in the first jaw 252 and through the end of the clevis 314. The first and second wires 306, 308 provide opening and closing forces to actuate the first and second jaws 252, 254.

As best seen in FIG. 5, the guide way 500 guides the wire 308 along a curved path that changes the direction of the wire by roughly 90°. Each of the first and second jaws 252, 254 includes a face 502 that is perpendicular to the first and second pivots 302, 304. The guide way includes a groove 500 in the face 502. In the embodiment shown, the wire is stranded to increase the flexibility and facilitate the ability of the wire to follow the curved path. In other embodiments, a solid wire is used to provide greater strength for a given cross-section size of the wire.

In one embodiment, the surgical end effector further includes two liners. Each liner is coupled to a face of one of the jaws and fitted within the groove 500 that forms the guide way. Thus the guide ways include a portion of the liners. The liners reduce the friction as the wires 306, 308 slide within the guide ways. The liners also electrically isolate the wires 306, 308 from the jaw through which they slide. The liners are further described and illustrated below for the embodiment shown in FIGS. 7-10.

The arrangement of the wires 306, 308 causes tension in each wire to apply a closing force to both jaws 252, 254. For example, when tension is applied to the second wire 308, the coupling 312 to the second jaw 254 will pull on the jaw to close it. At the same time, the tension applied to the second wire 308 will create a closing force on the first jaw 252 because of the forces created in the guide way as the second wire is turned by the guide way. Likewise, a compression force applied to each wire creates an opening force on both jaws 252, 254. This wire arrangement permits higher opening and closing forces to be generated by a more compact end effector.

In the embodiment shown, the first and second jaws 252, 254 and the first and second wires 206, 208 are electrically conductive. The clevis 300 and the first and second pivots 302, 304 are electrically non-conductive. This allows an electrical current to be supplied to the first and second jaws 252, 254 by the first and second wires 206, 208 for the purpose of performing bipolar electrocautery in which a tissue is cauterized by the current flowing from one jaw to the other through the tissue.

Figure 6:
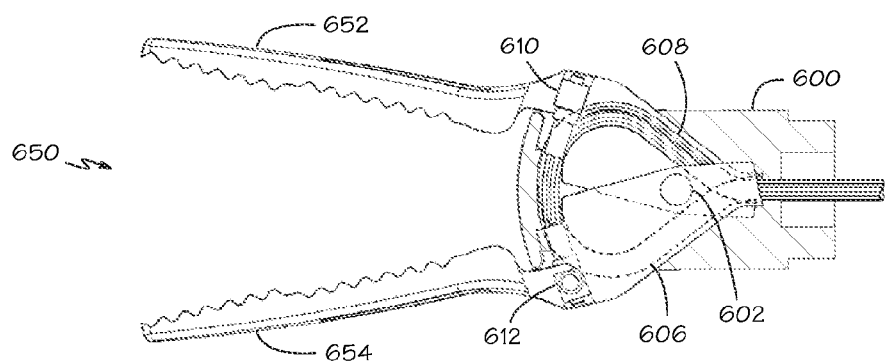
FIG. 6 is a front view of another surgical end effector.
Figure 7:
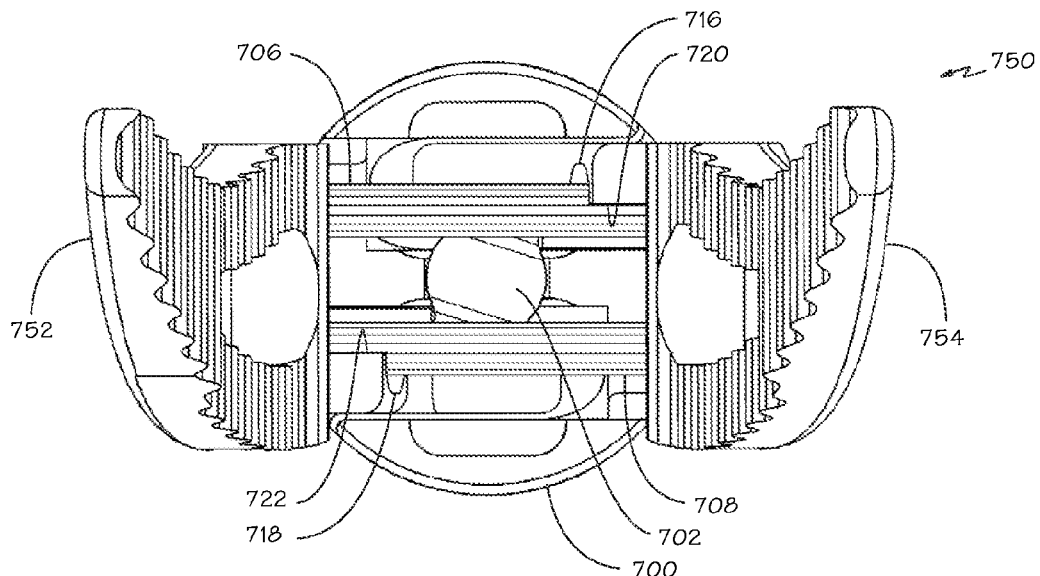
FIG. 7 is an end view of yet another surgical end effector.

FIG. 6 shows a top view of another surgical end effector 650. As in the previously described end effector, first and second wires 606, 608 are coupled 610, 612 to first and second jaws 652, 654 supported by a clevis 600 to provide the opening and closing forces. In this embodiment the first and second pivots 602 are joined together coaxially and are provided as a single element of the device.

FIGS. 7 through 10 show another surgical end effector 750. As in the previously described end effectors, first and second wires 706, 708 provide the opening and closing forces for the first and second jaws 752, 754. The guide ways 716, 718 in the faces 720, 722 of the jaws 752, 754 can be seen in FIG. 7. In this embodiment a rocking pin 702 is pivotally supported by the clevis 700. The rocking pin 702 is pivotally coupled to the first and second jaws 752, 754 such that the rocking pin constrains the first and second jaws to have opposite motions.

Figure 8A:
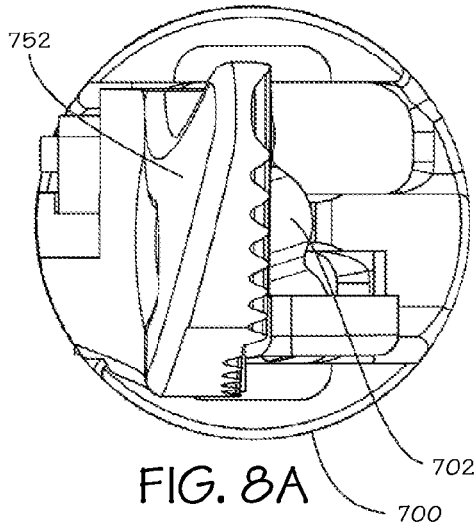
FIG. 8A is an end view of the surgical end effector of FIG. 7 in a closed position with one jaw removed to allow certain details to be seen more clearly.
Figure 9:
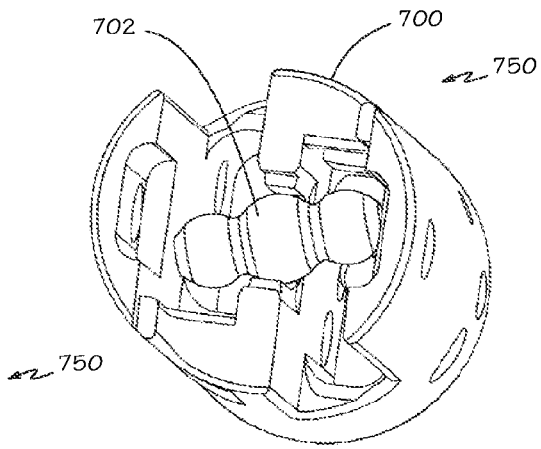
FIG. 9 is a perspective view of the surgical end effector of FIG. 7 in a closed position with both jaws removed.
Figure 8B:
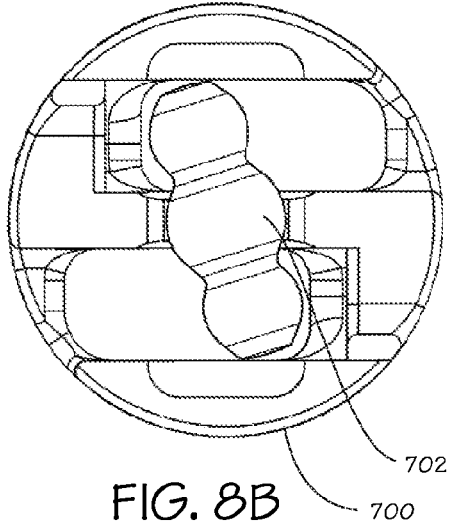
FIG. 8B is an end view of the surgical end effector of FIG. 7 in a closed position with both jaws removed to allow certain details to be seen more clearly.
Figure 10:
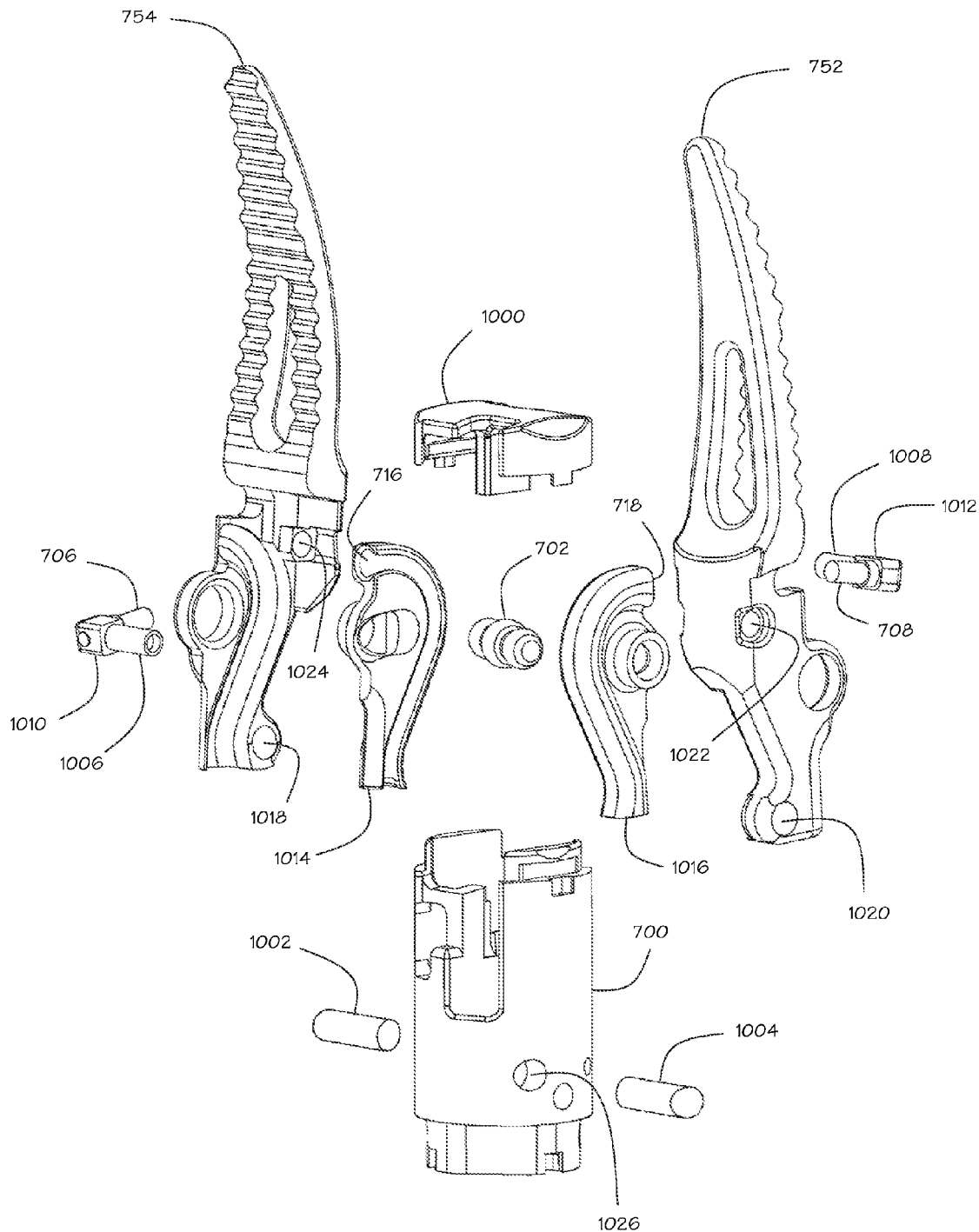
FIG. 10 is an exploded view of the surgical end effector of FIG. 7.

FIG. 8A shows the surgical end effector 750 in a closed position with one of the two jaws removed so that the rocking pin 702 can be partially seen. FIG. 8B shows the surgical end effector 750 in a closed position with both jaws removed so that the rocking pin 702 can be clearly seen. FIG. 9 shows the surgical end effector 750 in a perspective view that allows the relationship between the clevis 700 and the rocking pin 702 to be seen more clearly. FIG. 10 shows the surgical end effector 750 in an exploded view that allows the parts of the end effector to be seen more clearly. In the embodiment shown, the rocking pin 702 is pivotally supported by the clevis 700 at its midpoint. Therefore the rocking pin constrains the first and second jaws to have equal and opposite motions. In other embodiments, the rocking pin 702 is pivotally supported by the clevis 700 at other positions so that there is a ratio between the amount of the movement of each jaw other than 1:1.

The first and second jaws 752, 754 and the first and second wires 706, 708 can be electrically conductive. In the embodiment shown, a connector 1010, 1012 is crimped onto an end of each wire 706, 708. Each connector 1010, 1012 includes a shank 1006, 1008 that engages an opening 1022, 1024 in the jaw 752, 754 to provide both a mechanical and an electrical connection. The end of the shank 1006, 1008 is expanded after being inserted in the opening 1018, 1020 in the jaw 752, 754 to make a tight connection between the wire and the jaw. This allows an electrical current to be supplied to the first and second jaws 752, 754 by the first and second wires 706, 708 for the purpose of performing bipolar electrocautery in which a tissue is cauterized by the current flowing from one jaw to the other through the tissue.

Bipolar electrocautery requires that the first and second jaws 752, 754 be electrically isolated from one another except for the conductive path formed between the jaws when grasping a tissue. In the embodiment shown, the clevis 700 and the cap 1000 that encloses the moving parts within the clevis are electrically non-conductive. It is also necessary that the rocking pin 702 be prevented from providing a conductive path between the jaws 752, 754. This can be accomplished by making the rocking pin 702 from a non-conductive material. In the embodiment shown, non-conductive liners 1014, 1016 are added to provide the faces of the first and second jaws 752, 754. The liners 1014, 1016 interrupt the conductive path between the jaws 752, 754 and allow the rocking pin 702 to be made of metal.

The liners 1014, 1016 further provide the guide ways 716, 718 that support the wires 706, 708. The liners 1014, 1016 can be constructed of a plastic material with guide ways 716, 718 that reduce the friction on the insulating jacket on the wires 706, 708. In the embodiment shown, the guide ways 716, 718 surround somewhat more than half of the circumference of the wire in the guide way. In other embodiments, the guide ways completely surround the wire in the guide way. In still other embodiments, the guide ways surround half of the circumference of the wire in the guide way or somewhat less.

Figures 11A, 11B, 11C, 11D:
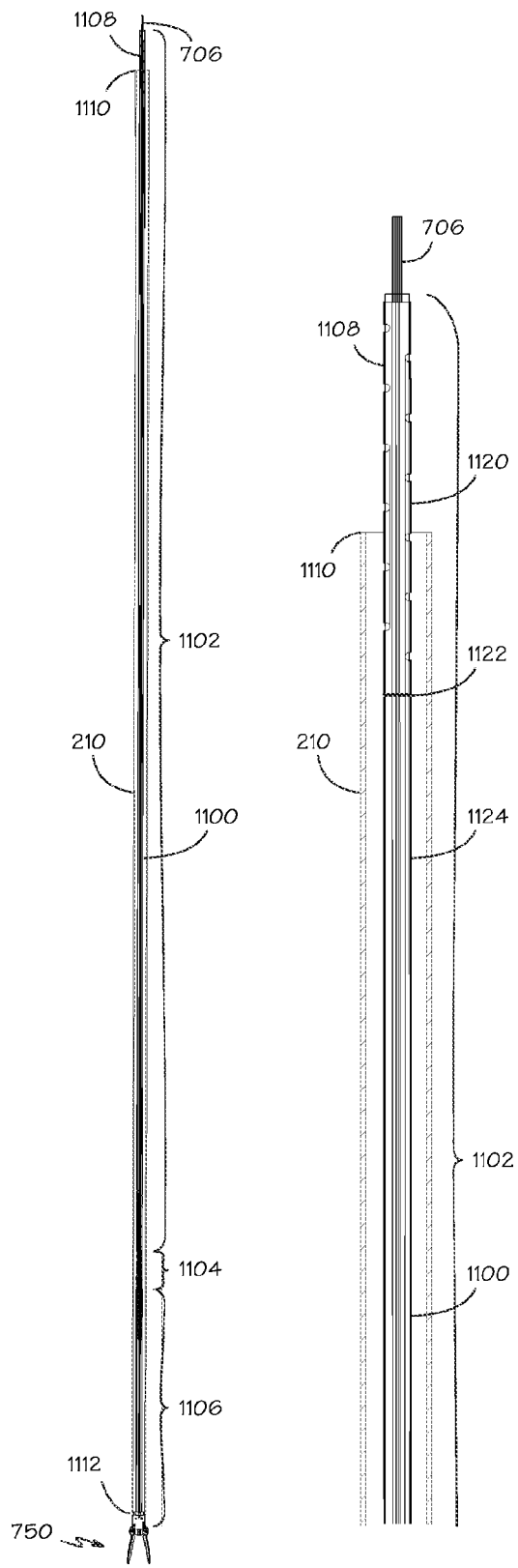
FIG. 11A is a front view of a minimally invasive surgical instrument with an elongate shaft shown in a section to allow certain details to be seen more clearly.
FIG. 11B is a detailed view of a proximal end of the minimally invasive surgical instrument shown in FIG. 11A.
FIG. 11C is a detailed view of a central portion of the minimally invasive surgical instrument shown in FIG. 11A.
FIG. 11D is a detailed view of a distal end of the minimally invasive surgical instrument shown in FIG. 11A.

FIG. 11A shows the elongate shaft 210 of the minimally invasive surgical instrument 120 shown in FIG. 2. FIGS. 11B through 11D show portions of the elongate shaft 210 in greater detail. It will be appreciated that FIGS. 11B through 11D do not collectively show the entire length of the elongate shaft 210, and that there are overlapping portions between these figures. The surgical end effector 750 shown in FIGS. 7-10 is shown coupled to a distal end 1112 of the elongate shaft 210 as an exemplary end effector. It will be appreciated that any embodiment of the end effector can be used with the elongate shaft 210.

The elongate shaft 210 includes a distal end 1112, a proximal end 1110, and a longitudinal axis extending between the distal end and the proximal end. The longitudinal axis is the axis of rotation, or axis of symmetry, of the elongate shaft 210. The clevis 700 of the end effector 250 is coupled to the distal end 1112 of the elongate shaft 210. As described above, the first and second jaws 752, 754 are pivotally coupled to the clevis 700. The first and second wires 706, 708 emerge from the end 1114 of the clevis as described above and extend through the elongate shaft 210 along the longitudinal axis between the distal end 512 and the proximal end 510. In one embodiment, the elongate shaft has a relatively small diameter of perhaps 5 to 6 mm.

In one embodiment, the first and second wires 706, 708 are of a stranded construction to provide the flexibility required to slide within the guide ways 716, 718 of the jaws 752, 754. The wires are constructed of a material such as nitinol or tungsten that provides high strength so that the cross-section of the wire can be minimized. The wire material and construction is also chosen to be durable through the repeated bending cycles imposed by sliding the wire through the curved guide way as the jaws as the end effector are opened and closed. In one embodiment the wires are insulated so that the only conductive metal exposed on them is at the distal end where it attached to the jaw, and at the proximal end where it is crimped into a connector pin. In one embodiment the insulation is ethylene tetrafluoroethylene (ETFE such as Tefzel® 750).

It will be appreciated that it is necessary to transmit a compressive force through the wires to provide an opening force for the jaws of the end effector. It will be further appreciated that it is necessary to support the wires so that the wires are able to transmit a compressive force without buckling. It is desirable to minimize the unsupported length of each wire to allow a higher compressive load to be applied without buckling the cable. For example, for a typical wire configuration that might be used in a 5 to 6 mm diameter elongate shaft, it is desirable to keep the unsupported length of wire less than one quarter of an inch and still more desirable to have a maximum unsupported length closer to $\frac{1}{16}$ of an inch. Therefore the minimally invasive surgical instrument 120 includes a wire guide 1100 coupled to the clevis 700 and to the first and second wires 706, 708 along the longitudinal (end to end) axis of the elongate shaft 210. The wire guide 1100 supports the first and second wires 706, 708 such that the first and second wires are able to transmit a compressive force without buckling.

The wire guide 1100 includes a proximal section 1102 adjacent the proximal end 1110 of the elongate shaft 210, a working section 1106 adjacent the working (distal) end 1112 of the elongate shaft 210, and a compression section 1104 coupled between the proximal section and the working section.

At least a portion of the proximal section 1102 of the wire guide 1100 is fixed to the first and second wires 706, 708 so that forces can be applied to the wires by gripping the proximal section and applying the forces to the proximal section. In the embodiment shown, a portion 1108 of the proximal section 1102 of the wire guide 1100 extends beyond the proximal end 1110 of the elongate shaft 210 to facilitate gripping the proximal section. In one embodiment, the proximal section 1102 of the wire guide 1100 includes an outer metal tube with a wire support inserted into the tube. The first and second wires 706, 708 pass through openings in the wire support. In one embodiment, the wire support is made of fluorinated ethylene propylene, (Teflon®-FEP or FEP). FEP melts at substantially the same temperature as ETFE allowing heat to be used to join together the wire insulation, wire support, and the metal tube. The FEP comes through slots in the metal, creating a mechanical connection. In this way, the wires 706, 708 can be mechanically driven by grabbing the metal tube while keeping the wires electrically isolated.

FIG. 12 shows a side view of the portion 1108 of the proximal section 1102 of the wire guide 1100 that extends beyond the proximal end 1110 of the elongate shaft 210. The first and second wires 706, 708 extend from the wire guide to facilitate making electrical connections to the cables.

Referring again to FIG. 11B, in the embodiment shown the elongate shaft 210 rotates relative to the proximal control mechanism 240 (FIG. 2) to provide an additional motion of the end effector 750. The proximal section 1102 of the wire guide 1100 is made in two pieces 1120, 1124. The upper piece 1120 of the proximal section 1102 is held in a fixed position relative to the proximal control mechanism 240 to accommodate the gripping of the proximal section and the electrical connections to the cables. The lower piece 1124 of the proximal section 1102 is coupled to the elongate shaft 210 to rotate with it. The two pieces 1120, 1124 rotate relative to each other at the joint 1122 between the pieces. The wire insulation, wire support, and the metal tube are joined together at the distal end of each of the two pieces 1120, 1124. This leaves a long length of the wires 706, 708 that can twist within the lower piece 1124 of the proximal section 1102 as the elongate shaft 210 rotates. The upper piece 1120 in the embodiment shown is about 4 inches long and the lower piece 1124 is about 16 inches long.

The distal end of the working section 1106 of the wire guide 1100 is fixed to the clevis 700 of the end effector 750. The wires 706, 708 slide within grooves in the working section 1106 parallel to the longitudinal axis of the elongate shaft 210. In one embodiment, the working section 1106 provides lateral flexibility to accommodate flexibility and/or articulation in the elongate shaft 210.

If a portion of the proximal section 1102 of the wire guide 1100 is fixed to the first and second wires 706, 708, then the overall length of the wire guide 1100 will change as forces are applied to the wires by applying the forces to the proximal section. The compression section 1104 coupled to the proximal section 1102 and the working section 1106 accommodates these changes in length while providing support for the wires to prevent buckling.

FIG. 11C shows the portion of the elongate shaft 210 that includes the compression section 1104 of the wire guide 1100. FIG. 13A shows a portion of the compression section in an uncompressed condition. FIG. 13B shows a portion of the compression section in a compressed condition. FIG. 14 shows a perspective view of a wire support section 1300 that is used to form the compression section 1104.

In the embodiment shown, the compression section 1104 is formed by coupling a number of wire support sections 1300 with compression springs 1306. As best seen in FIGS. 13A and 14, the wires 706, 708 pass-through guideways 1402, 1404 in the wire support section 1300 and are further supported by the compression springs 1306 that connect the support sections. The compression section 1104 of the wire guide 210 allows the wire guide to change length as the proximal section 1102 is moved to apply forces through the wires 706, 708. The compression section 1104 allows the wire guide 1100 to be reduced in length when a compression force is applied to the proximal section 1102. This feature allows a compression force to be applied to the wires 706, 708 while providing the support necessary to prevent buckling of the cables.

As may be seen in FIG. 13A, the length of the compression springs 1306 when uncompressed is chosen to be twice the length of the portion 1406 of the wire support section 1300 to which the spring is coupled plus the desired maximum unsupported length of the cable.

As may be seen in FIG. 13B, the compression springs 1306 may be compressed to the point where the end face 1304 of one wire support section 1300 contacts the opposing end face 1302 of an adjacent wire support section. Thus each compression spring 1306 allows a change of length roughly equal to the unsupported length when the spring is uncompressed. Any desired number of compression sections 1300 can be used to form the compression section 1104 to provide the desired travel of the proximal section 1102 relative to the working section 1106.

FIGS. 15 through 17 show details of the coupling of the end effector 750 to the distal end 1112 of the elongate shaft 210. FIG. 15 is a top view of the elongate shaft 210 with the wire guide 1100 shown along the longitudinal axis. FIG. 16 is a front view of the end effector 750 coupled to the distal end 1112 of the elongate shaft 210 with the jaws 752, 754 in an open position. FIG. 17 is a section view of the end effector 750 taken along line 17-17 of FIG. 15 with the second jaw 754 not shown for clarity.

As best seen in FIG. 17, the clevis 700 of the end effector 750 is fixed to the end of the wire guide 1100. Thus a wire 708 slides through a guideway of a jaw 752, emerges from the end 1114 of the clevis 700, and extends through the wire guide 1100 to the proximal end 1110 of the elongate shaft 210. As previously described, an end 712 of the wire 708 is coupled to a first jaw 754 and then extends through a guideway of a second jaw 752 such that tension and compression of the wire creates closing and opening forces on the first and second jaws which are connected to the clevis 700 by pivots 704. A rocking pin 702 is pivotally supported by the clevis 700 and pivotally coupled to the first and second jaws 752, 754 such that the rocking pin constrains the first and second jaws to have equal and opposite motions.

Figures 18, 19:
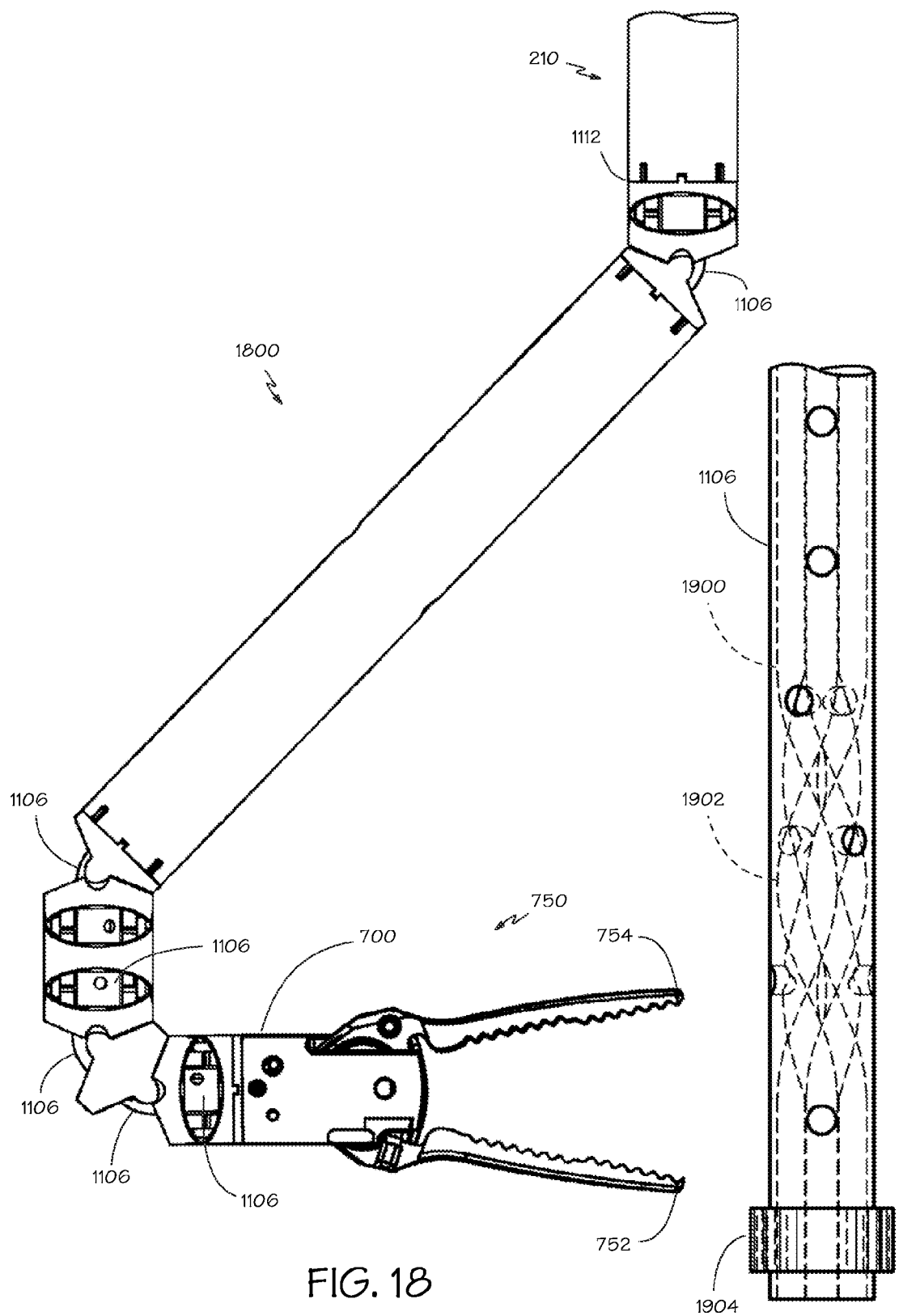
FIG. 18 is a front view of an end effector with an articulated wrist.
FIG. 19 is a detailed view of a distal section of the wire guide.

FIG. 18 is a front view of the end effector 750 coupled to the distal end 1112 of the elongate shaft 210 by an articulated wrist assembly 1800. The distal end of the working section 1106 of the wire guide 1100 passes through the articulated wrist assembly 1800 along its central axis and is fixed to the clevis 700 of the end effector 750. The wires 706, 708 slide within grooves in the working section 1106 parallel to the longitudinal axis of the elongate shaft 210. The working section 1106 provides lateral flexibility to accommodate the movement at the joints of the articulated wrist assembly 1800. In the embodiment shown, the distal end of the working section 1106 includes perforations in the outer tube at least at the most distal portion to allow fluids to drain from the wire guide 1100. As may be seen in FIG. 11C, in some embodiments portions of the working section 1106 are provided with a protective covering, such as spring wire, to protect the guide from abrasion where it passes through articulated joints. Other forms of articulated wrist assemblies with greater or fewer degrees of freedom may also be used to couple the end effector to the distal end of the elongate shaft.

FIG. 19 is a detailed view of a distal section of the wire guide. In the embodiment shown, the guideways 1900, 1902 for the two wires provide a 360 degree twist in the portion of the wire guide that passes through the wrist. This tends to compensate for the slight differences in path length that result from bending of the wire guide as the wrist is articulated. An enlarged portion 1904 of the wire guide is coupled to the distal part of the instrument so that the wire guide 1106 can't rotate or pull away from the clevis 750.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

What is claimed is:

1. A surgical end effector comprising:
   a clevis;
   a first jaw;
   a first pivot that couples the first jaw to the clevis;
   a second jaw;
   a second pivot that couples the second jaw to the clevis;
   a first wire coupled to the first jaw to transmit a controller motion to the first jaw and to the second jaw;
   a second wire coupled to the second jaw to transmit the controller motion to the second jaw and to the first jaw;
   a first guide way in the first jaw, the first guide way being a first curved path that extends from the second jaw to the clevis, changes direction by roughly ninety degrees, and includes a continuous first surface that extends from the second jaw to the clevis along the inside of the first curved path, the second wire extending in the first guide way along the first surface to the second jaw; and a second guide way in the second jaw, the second guide way being a second curved path that extends from the first jaw to the clevis, changes direction by roughly ninety degrees, and includes a continuous second surface that extends from the first jaw to the clevis along the inside of the second curved path, the first wire extending in the first guide way along the second surface to the first jaw.

2. The surgical end effector of claim 1 wherein the first and second pivots are coaxial.

3. The surgical end effector of claim 1 further comprising a rocking pin pivotally supported by the clevis and pivotally coupled to the first and second jaws such that the rocking pin constrains the first and second jaws to have opposite motions.

4. The surgical end effector of claim 1 wherein the first guide way and the second guide way each include a groove defined in a face perpendicular to the pivot axis of the pivots.

5. The surgical end effector of claim 4 further comprising a first and a second liner, each liner fitted within the groove of one of the first guide way and the second guide way, the guide ways including a portion of the liners.

6. The surgical end effector of claim 1 wherein the first and second jaws and the first and second wires are electrically conductive, and the clevis is electrically non-conductive.

7. The surgical end effector of claim 6 further comprising electrically non-conductive liners coupled to the first and second jaws and a rocking pin pivotally supported by the clevis and pivotally coupled to the first and second jaws such that the rocking pin constrains the first and second jaws to have opposite motions, the rocking pin being electrically isolated from the first and second jaws by the liners.

8. A minimally invasive surgical instrument comprising:
   an elongate shaft having a distal end, a proximal end, and a longitudinal axis extending between the distal end and the proximal end;
   an end effector having a clevis coupled to the distal end of the elongate shaft, a first jaw pivotally coupled to the clevis, and a second jaw pivotally coupled to the clevis;
   a first wire coupled to the first jaw to transmit a controller motion to the first jaw and to the second jaw, the first wire extending through a second guide way in the second jaw and through the elongate shaft between the distal end and the proximal end, the second guide way being a second curved path that extends from the first jaw to the clevis, changes direction by roughly ninety degrees, and includes a continuous second surface that extends from the first jaw to the clevis along the inside of the second curved path; and
   a second wire coupled to the second jaw to transmit the controller motion to the second jaw and to the first jaw, the second wire extending through a first guide way in the first jaw and through the elongate shaft between the distal end and the proximal end, the first guide way being a first curved path that extends from the second jaw to the clevis, changes direction by roughly ninety degrees, and includes a continuous first surface that extends from the second jaw to the clevis along the inside of the first curved path.

9. The minimally invasive surgical instrument of claim 8 wherein the end effector further has a rocking pin pivotally supported by the clevis and pivotally coupled to the first and second jaws such that the rocking pin constrains the first and second jaws to have opposite motions.

10. The minimally invasive surgical instrument of claim 8 wherein each of the first and second jaws includes a face that is perpendicular to the pivotal coupling, the first guide way including a groove in the face of the first jaw, the second guide way including a groove in the face of the second jaw.

11. The minimally invasive surgical instrument of claim 10 wherein the first and second jaws and the first and second wires are electrically conductive, and the clevis is electrically non-conductive, such that the first jaw and first wire are electrically isolated from the second jaw and second wire.

12. The minimally invasive surgical instrument of claim 11 further comprising electrically non-conductive liners, each liner fitted within the groove of one of the first guide way and the second guide way, the guide ways including a portion of the liners, and a rocking pin pivotally supported by the clevis and pivotally coupled to the first and second jaws such that the rocking pin constrains the first and second jaws to have opposite motions, the rocking pin being electrically isolated from the first and second jaws by the liners.

13. The minimally invasive surgical instrument of claim 8 further comprising a wire guide coupled to the clevis and to the first and second wires along the longitudinal axis of the elongate shaft, the wire guide supporting the first and second wires such that the first and second wires are able to transmit a compressive force without buckling.

14. The minimally invasive surgical instrument of claim 13 wherein the wire guide includes a proximal section adjacent the proximal end of the elongate shaft, a working section adjacent the distal end of the elongate shaft, and a compression section coupled to the proximal section and the working section, the compression section including a plurality of wire support sections coupled to a compression spring such that the wire guide is reduced in length when a compression force is applied.

15. The minimally invasive surgical instrument of claim 8 wherein the end effector further including means for constraining the first and second jaws to have opposite motions.

16. The minimally invasive surgical instrument of claim 15 further comprising means for electrically isolating the first jaw and wire from the second jaw and cable.

17. The minimally invasive surgical instrument of claim 8 further comprising means for preventing buckling of the first and second wires when transmitting a compressive force.

18. The minimally invasive surgical instrument of claim 17 wherein the means for preventing buckling is shortened when transmitting the compressive force.

19. A surgical end effector comprising:
   a clevis;
   a first jaw rotatably coupled to the clevis by a first pivot, the first jaw having a first face perpendicular to the axis of rotation of the first pivot and a first guide way, the first guide way being a first curved path in the first face that extends from the clevis, changes direction by roughly ninety degrees, and includes a continuous first surface that extends from the second jaw to the clevis along the inside of the first curved path;
   a second jaw rotatably coupled to the clevis by a second pivot, the second jaw having a second face perpendicular to the axis of rotation of the second pivot and a second guide way, the second guide way being a second curved path in the second face that extends from the first jaw to the clevis, changes direction by roughly ninety degrees, and includes a continuous second surface that extends from the first jaw to the clevis along the inside of the second curved path;

a first wire coupled to the first jaw to transmit a controller motion to the first jaw and to the second jaw and extending through the second guide way to the clevis; and a second wire coupled to the second jaw to transmit the controller motion to the second jaw and to the first jaw and extending through the first guide way to the clevis.

\* \* \* \* \*